United States Patent [19]

Clanton

[11] 4,177,871

[45] Dec. 11, 1979

[54] TOY STETHOSCOPE

[75] Inventor: W. Porter Clanton, East Aurora, N.Y.

[73] Assignee: The Quaker Oats Company, Chicago, Ill.

[21] Appl. No.: 860,696

[22] Filed: Dec. 15, 1977

[51] Int. Cl.$^2$ .......................... A61B 7/02; H04R 25/00
[52] U.S. Cl. ...................................... 181/131; 181/137
[58] Field of Search .............................. 181/131–137, 181/129

[56] References Cited

U.S. PATENT DOCUMENTS

| 350,393 | 10/1886 | Radzinsky | 181/131 |
| 1,832,422 | 11/1931 | Pilling | 181/137 |
| 1,964,604 | 6/1934 | Swickard | 181/137 |

FOREIGN PATENT DOCUMENTS 259326  10/1926  United Kingdom ...................... 181/131

Primary Examiner—Stephen J. Tomsky
Attorney, Agent, or Firm—Cumpston & Shaw

[57] ABSTRACT

A toy stethoscope having a resilient sound collector at one end thereof. The sound collector is soft and pliable so as to prevent injury to a person in the event the person is struck by the sound collector. The sound collector further comprises a damper formed from a soft sponge or foam material that prevents unpleasant pressure and/or injury to the ear drums in the event a loud sound is introduced into the sound collector due to someone yelling or blowing directly into the collector or the like.

5 Claims, 4 Drawing Figures

TOY STETHOSCOPE

BACKGROUND OF THE INVENTION

1. Field of the Invention

This invention relates generally to stethoscopes, and more particularly to a resilient sound collector for a stethoscope.

2. Description of the Prior Art

All stethoscopes have a pair of ear pieces at one end insertable into the ears of a user, a sound collector at the other end placeable on the surface of a sound producing body, and a pair of sound conducting tubes connecting the sound collector to the ear pieces for conducting the sound waves to the ear drums of the user. The sound collectors and disk-like diaphragms contained therein have heretofore been formed out of hard material such as metal. Although such sound collectors operate satisfactorily for adult use, they create a serious problem when used in toy stethoscopes handled by children. Children tend to be less careful than adults and are prone, for example, to swing the stethoscope about without too much concern for other persons near by or to yell into the diaphragm of the sound collector. A sound collector formed from hard material when swumg haphazardly can inflict serious injury to others, particularly if one is struck in the eye. Also, yelling into the diaphragm of the sound collector or tapping the diaphragm sharply can crease unpleasant pressure, noise and/or damage to the ear drums of the user. Applicant's invention is believed to obviate these and other disadvantages of prior art sound collectors.

SUMMARY OF THE INVENTION

In accordance with a preferred embodiment of the invention, a resilient sound collector for a toy stethoscope is disclosed. The resilient sound collector comprises in one aspect a body formed of soft sponge or foam material. In another aspect of the invention, the sound collector comprises a cup-shaped housing formed from a soft pliable material, and a damper supported thereby formed from a soft sponge or foam material.

In a more specific aspect of the invention, the cup-shaped housing is circular and has a peripheral sound sealing rim. The housing further has a central blind bore having a recess extending from a bottom surface thereof with which open ends of a pair of sound conducting tubes communicate. A cylindrical damper formed of a soft sponge or foam material is inserted into the blind bore and secured to the bottom surface thereof.

One of the advantages of the resilient sound collector of this invention is to prevent injury to any person struck by the sound collector when it is carelessly and haphazardly swung to and fro. An advantage of forming the damper of the sound collector from a soft sponge or foam material is to allow sufficient sound collection for use as a stethoscope while preventing unpleasant pressure on and/or damage to the ear drums of a user in the event a person yells or blows into the damper, or it is rapped or struck sharply with a finger or other object such as a pencil. The sponge or foam material tends to diffuse the sound waves and lessens the impact of the sound on the ear drums.

The invention and its advantages will become more apparent from the detailed description of the preferred embodiment presented below.

BRIEF DESCRIPTION OF THE DRAWING

In the detailed description of the preferred embodiment of the invention presented below, reference is made to the accompanying drawing, in which.

DESCRIPTION OF THE PREFERRED EMBODIMENT

Figure 1:
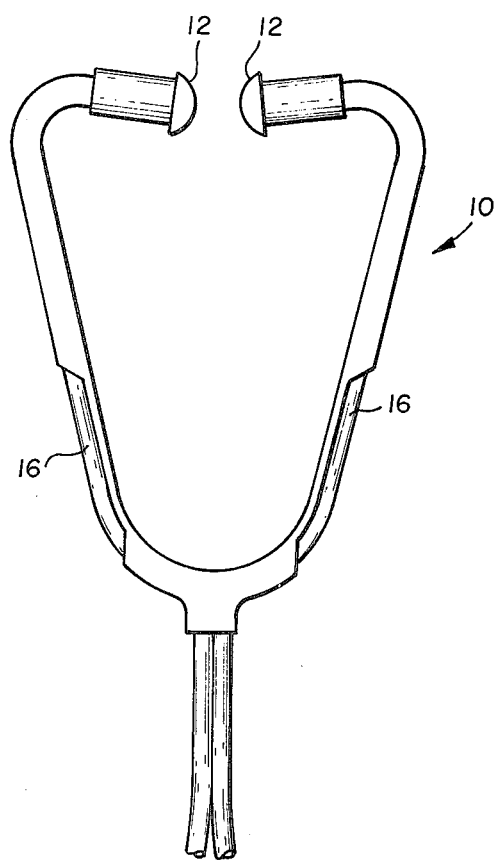
FIG. 1 is a front elevational view of a toy stethoscope of this invention in which a resilient sound collector is incorporated.

With reference to FIG. 1, a toy stethoscope 10 is disclosed comprising a pair of ear pieces 12 at one end insertable into the ears of a user. A resilient sound collector 14 which is manually pressed onto the surface of a sound producing body is attached to the opposite end of the stethoscope. A pair of sound wave conducting tubes 16 are provided having one of their ends connected to ear pieces 12 and the opposite ends connected to sound collector 14 for conducting sound waves from the collector to the ear pieces.

Figure 2:
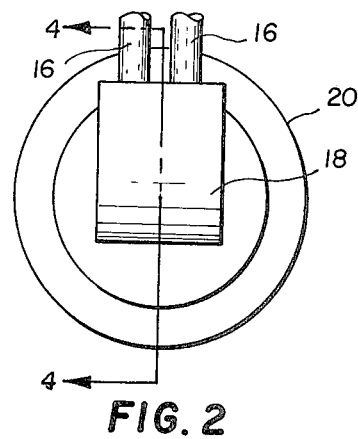
FIG. 2 is a rear elevational view of the sound collector of FIG. 1.
Figure 3:
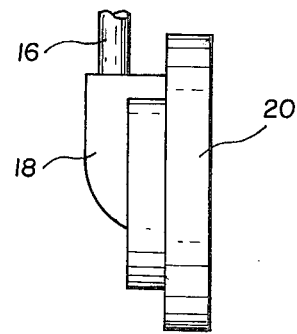
FIG. 3 is a side elevational view of the sound collector of FIG. 2.
Figure 4:
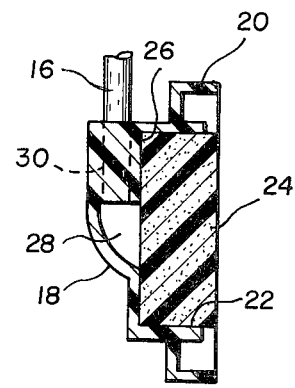
FIG. 4 is a section taken substantially along line 4—4 of FIG. 2.

The resilient sound collector 14 is more specifically disclosed in FIGS. 2-4. The sound collector comprises a cup-shaped housing 18 formed from any suitable soft pliable material, e.g. polymeric material such as plastic or rubber. Due to the soft and pliable nature of this material, anyone struck by sound collector 14 will not be injured or damaged thereby as would likely result if the sound collector were formed from a hard material such as metal or the like. The sound collector 14 has a peripheral sound sealing rim or lip 20 which when pressed into engagement with a sound producing body localizes the sound producing area. The housing 18 further has a central sound cavity 22 comprising a blind bore for receiving a pad or block of sound damper material such as a cylindrical damper 24. The damper is formed from a cellular material such as a soft sponge rubber or plastic foam material which allows sufficient sound collection for use in a stethoscope. The soft sponge or foam material is believed to diffuse sound waves and prevent unpleasant pressure or damage to the ear drums of the user in the event anyone blows, yells or strikes the damper with a hard object such as a finger or pencil. The damper 24 further nests within sound cavity 22 with the lower surface thereof secured to the bottom surface 26 of the cavity by any suitable adhesive or the like. A recess or opening 28 extends from bottom surface 26 of sound cavity 22. End portions 30 of sound conducting tubes 16 are embedded in housing 18 with the open ends thereof extending into or terminating at recess 28 to provide communication therebetween.

The invention has been described in detail with particular reference to a preferred embodiment, but it will be understood that variations and modifications can be effected within the spirit and scope of the invention as described hereinabove.

What is claimed is:

1. A toy stethoscope for conducting sound comprising:

a pair of flexible sound conducting tubes;

an ear piece connected to one end portion of each of said tubes; and a soft pliable housing secured to the opposite end portions of said tubes, said housing having a substantially blind bore extending from one end thereof in which the blind end of said bore has at least one opening communicating with the open ends of said opposite end portions of said tubes, said housing further having a pad or block of soft sound damper material mounted within said blind bore and overlying said opening in said blind end for damping the sound conducted through said blind bore and said tubes to said ear pieces.

2. The stethoscope of claim 1 wherein said pad or block is formed from a cellular damper material such as plastic foam extending substantially across and substantially closing said blind bore.

3. The stethoscope of claim 2 wherein said housing further has a sound sealing lip encircling said one end of said housing.

4. The stethoscope of claim 2 wherein said one end of said housing is cylindrical, said lip is cylindrical and radially spaced from said one end of said housing, and the free end surface of said lip and the outer side surface of said damper material lie substantially in the same plane.

5. The stethoscope of claim 1 wherein said one end of said housing is cylindrical, said blind bore is cylindrical, said pad is formed from a cellular damper material such as plastic foam which is cylindrical and mounted within and extends substantially across and substantially fills said blind bore with a portion of the inner surface of said pad in engagement with said blind end, and further having a cylindrical sound sealing lip encircling said one end of said housing and radially spaced therefrom, and the free end surface of said lip and the outer surface of said pad lie substantially in the same plane.

* * * * *